United States Patent [19]

Schönbeck et al.

[11] 4,058,390
[45] Nov. 15, 1977

[54] AMINE SALTS OF PHENYL-4-HYDROXYPYRIDAZINES AND THE PREPARATION AND HERBICIDAL COMPOSITIONS THEREOF

[75] Inventors: Rupert Schönbeck, Leonding; Engelbert Kloimstein, Eferding; Erwin Wittmann, Linz, all of Austria

[73] Assignee: Chemie Linz Aktiengesellschaft, Linz, Austria

[21] Appl. No.: 641,588

[22] Filed: Dec. 16, 1975

[30] Foreign Application Priority Data

Dec. 17, 1974  Austria .............................. 10073/74

[51] Int. Cl.² .................... A01N 9/24; C07D 237/14
[52] U.S. Cl. .................................. 71/92; 260/250 A; 260/250 AH; 71/90; 544/109
[58] Field of Search ...................... 260/250 A; 71/92

[56] References Cited

U.S. PATENT DOCUMENTS

2,805,926  9/1957  Schoene ................................ 71/92
3,790,571  2/1974  Diskus .............................. 260/250 A

*Primary Examiner*—Alton D. Rollins
*Assistant Examiner*—Mark L. Berch
*Attorney, Agent, or Firm*—Wenderoth, Lind & Ponack

[57] ABSTRACT

Amine salts of 3-phenyl-6-halo-4-hydroxypyridazines of the formula:

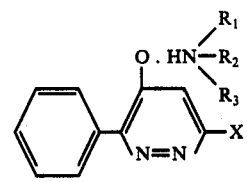

in which X is a chlorine or bromine atom, $R_1$ is an alkyl group containing up to 14 carbon atoms, which group may be substituted by a hydroxy group, an alkoxy group containing up to 10 carbon atoms, cyano group, amino group or lower mono- or lower dialkylamino group, an alkenyl group containing up to 6 carbon atoms or a cycloalkyl group containing 5, 6 or 7 carbon atoms, and $R_2$ and $R_3$ have the same meaning as $R_1$ or each is a hydrogen atom, or $R_1$ and $R_2$ together with the nitrogen atom of the amine form a 5- or 6-membered heterocyclic group which may also contain oxygen and which may be mono- or di- substituted by alkyl, and herbicidal compositions containing them.

16 Claims, No Drawings

AMINE SALTS OF PHENYL-4-HYDROXYPYRIDAZINES AND THE PREPARATION AND HERBICIDAL COMPOSITIONS THEREOF

The present invention relates to salts of phenylpyridazines and the preparation thereof. More particularly the invention is concerned with amine salts of 3-phenyl-6-halo-4-hydroxypyridazines having valuable herbicidal properties, the preparation of such salts and herbicidal compositions containing them.

From U.S. Pat. No. 3,790,571 it is known that phenylpyridazine derivatives of the general formula:

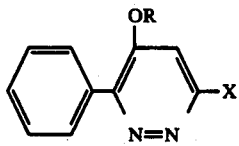

in which X is a chlorine or bromine atom and R is a hydrogen atom or a methyl or acetyl group, have herbicidal properties. In particular those derivatives in which R is a hydrogen atom have a very good herbicidal effect against a range of broad-leaved weeds when applied in an amount of 2.0 kg of active substance per hectare, while cultivated cereals are found to be tolerant towards these substances. This fact enables a selective control of broad-leaved weeds to be achieved.

In the copending application Ser. No. 415,555, filed Nov. 14, 1973 (U.S. Pat. No. 3,932,405), from two of the present inventors with others, phenylpyridazine derivatives of the general formula:

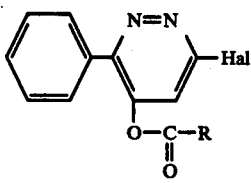

in which Hal is a chlorine or bromine atom and R is a straight-chain or branched alkyl group or the group OR' wherein R' is an alkyl group which may be straight-chain or branched are described and claimed, which have a very good herbicidal property. These compounds are costly to manufacture and readily decompose in the presence of water to give the free hydroxy compound and the corresponding acid component. This difficulty particularly arises when these esters are applied in the form intended for application, which is normally a solution or a suspension. The corresponding thioesters are described and claimed in the copending application Ser. No. 480,309, filed June 17, 1974 (U.S. Pat. No. 3,953,445), which have outstanding herbicidal properties, the stability of which is also not always satisfactory.

It has now been found that the amine salts of 3-phenyl-4-hydroxy-6-chloro(or bromo)-pyridazine have a substantially enhanced herbicidal effect compared with the corresponding free hydroxy compound, are easier to prepare compared with the compounds specified in copending application Ser. Nos. 415,555 now U.S. Pat. No. 3,932,405 and 480,309 now U.S. Pat. No. 3,953,445 and are more stable in solution or suspension. The enhanced herbicidal effect in comparison with the free hydroxy compound is surprising, particularly as the corresponding alkali metal or ammonium salts have only a slight herbicidal activity.

Accordingly the present invention provides an amine salt of a 3-phenyl-6-halo-4-hydroxypyridazine having the general formula:

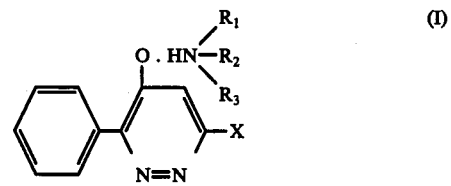

in which X is a chlorine or bromine atom and $R_1$ is an alkyl group containing up to 14 carbon atoms, which group may be substituted by a hydroxy group, an alkoxy group containing up to 10 carbon atoms, nitrile group, amino group or mono- or dialkylamino group in which the alkyl group has up to 6 carbon atoms, an alkenyl group containing up to 6 carbon atoms or a cycloalkyl group containing 5, 6 or 7 carbon atom and $R_2$ and $R_3$ have the same meaning as $R_1$ or each is a hydrogen atom, or $R_1$ and $R_2$ together with the nitrogen atom of the amine form a 5- or 6-membered heterocyclic group which may also contain oxygen and which may be mono- or disubstituted by alkyl, preferably lower alkyl.

Particularly preferred compounds are those of formula (I) in which X is a chlorine atom; and those wherein $R_1$ is an alkyl group of 2 to 10 carbon atoms, allyl, cyclohexyl, cyanoethyl, a hydroxyalkyl group of 2 to 4 carbon atoms or an alkoxyalkyl group with up to 6 carbon atoms in the alkoxy group and wherein each of $R_2$ and $R_3$ is a hydrogen atom, an alkyl group having 1 to 6 carbon atoms, allyl, hydroxyalkyl or cyanoethyl. When $R_1$ and $R_2$ together with the amino-nitrogen atom form a heterocyclic ring, the pyrrolidino, piperidino or morpholino group is then particularly preferred, and each of these groups is substituted by one or two methyl groups. $R_3$ is then preferably a hydrogen atom.

The present invention also provides a process for the preparation of a compound of formula (I), which comprises reacting 3-phenyl-6-chloro(or bromo)-4-hydroxypyridazine with an amine of the general formula

in which $R_1$, $R_2$ and $R_3$ are as defined above in formula (I), in approximately stoichiometric amounts at a temperature from room temperature to 100° C. Preferably the reaction may be carried out in the presence of a solvent.

The compounds according to the invention may be used as active ingredients in herbicidal compositions on account of their interesting herbicidal properties.

The formulation of herbicidal compositions containing the active ingredients of formula (I) is very simple. The amine salts are in general soluble in water, and some are also soluble in organic solvents. When using an organic solvent they very easily may be brought into an extremely finely divided form in water by adding emulsifiers and/or wetting agents.

A solid formulation may be obtained by simply mixing the amine salt with a solid diluent or diluting agent and adding a dispersing agent.

In contrast to this, the corresponding free hydroxy compound is practically insoluble in both water and organic solvents, and must therefore be ground to a very fine grain size before use.

Very favourable results are obtained if a mixture of amine salts of formula (I) is used as the active ingredient.

It is also possible to admix the agents according to the invention with other, known herbicidal agents, such as, in particular:
2,4-dichlorophenoxyacetic acid (2,4-D)
2-methyl-4-chlorophenoxyacetic acid (MCPA)
2,4,5-trichlorophenoxyacetic acid (2,4,5-T)
2-(2-methyl-4-chlorophenoxy)-propionic acid (CMPP)
2-(2,4-dichlorophenoxy)-propionic acid (2,4-DP)
4-(2-methyl-4-chlorophenoxy)-butyric acid (MCPB)
4-(2,4-dichlorophenoxy)-butyric acid (2,4-DB)
2-(2,4,5-trichlorophenoxy)-propionic acid (2,4,5-TP)
4-chloro-2-oxobenzothiazolin-3-yl acetic acid
3,6-dichloro-2-methoxybenzoic acid, and the amine salts or esters thereof, since the active ingredients according to the invention are not, in contrast to those disclosed in West German Offenlegungsschrift No. 2,256,172, sensitive to acids.

The amount applied is as a rule 1 to 2 kg/hectare.

The following Examples illustrate the invention and the manner in which it may be performed.

EXAMPLE 1

20.6 g of 3-phenyl-4-hydroxy-6-chloropyridazine were suspended in 100 ml of ethanol, 12.9 g of n-octylamine were added and the mixture was heated for a short time at 80° C. The solution formed was evaporated. 32.8 g of residue remained, which crystallised on cooling. After recrystallisation from ethyl acetate, 25.8 g of the n-octylamine salt of 3-phenyl-4-hydroxy-6-chloropyridazine were obtained, having a melting point of 90° to 95° C.

| C | calculated | 64.56% | H | calculated | 7.53% | N | calculated | 12.55% |
|---|---|---|---|---|---|---|---|---|
|   | found | 63.9% |   | found | 7.7% |   | found | 12.1% |
| Cl | calculated | 10.59% | O | calculated | 4.78% |   |   |   |
|   | found | 10.2% |   | found | 5.0% |   |   |   |

EXAMPLE 2

20.6 g. of 3-phenyl-4-hydroxy-6-chloropyridazine were suspended in 100 ml. of water, 8.4 g. of N-methyl-N-$\beta$-cyanoethylamine were added, and the mixture was heated for 15 minutes at 80° C. The reaction mixture was then cooled, the crystalline product was suction filtered, dried and recrystallised from ethyl acetate. 26.6 g. of the N-methyl-N-$\beta$-cyanoethylamine salt of 3-phenyl-4-hydroxy-6-chloropyridazine were obtained, having a melting point of 110° C.

| C | calculated | 57.83% | H | calculated | 5.20% | N | calculated | 19.27% |
|---|---|---|---|---|---|---|---|---|
|   | found | 57.6% |   | found | 5.1% |   | found | 19.0% |
| Cl | calculated | 12.20% | O | calculated | 5.50% |   |   |   |
|   | found | 12.0% |   | found | 6.0% |   |   |   |

EXAMPLE 3

20.6 g. of 3-phenyl-4-hydroxy-6-chloropyridazine were suspended in 100 ml. of xylene, 11.3 g of N-methyl-N-cyclohexylamine were added, and the mixture was heated for 15 minutes at about 90° C. while stirring.

The oil formed was separated, acetone was added, and the crystalline product formed was suction filtered and dried.

27.4 g. of the N-methyl-N-cyclohexylamine salt of 3-phenyl-4-hydroxy-6-chloropyridazine were obtained, having a melting point of 110° – 112° C.

| C | calculated | 63.84% | H | calculated | 6.93% | N | calculated | 13.14% |
|---|---|---|---|---|---|---|---|---|
|   | found | 64.1% |   | found | 6.0% |   | found | 13.1% |
| Cl | calculated | 11.09% | O | calculated | 5.0% |   |   |   |
|   | found | 11.0% |   | found | 5.2% |   |   |   |

The following compounds, for example, of the formula I can also be obtained:

N-n-propyl-N-$\beta$-cyanoethylamine salt of 3-phenyl-4-hydroxy-6-chloropyridazine.

Melting point: from 150° C, with decomposition

| C | calculated | 60.28% | H | calculated | 6.01% | N | calculated | 17.58% |
|---|---|---|---|---|---|---|---|---|
|   | found | 59.9% |   | found | 6.0% |   | found | 17.4% |
| Cl | calculated | 11.12% | O | calculated | 5.02% |   |   |   |
|   | found | 11.1% |   | found | 5.3% |   |   |   |

N-isopropyl-N-2-cyanoethylamine salt of 3-phenyl-4-hydroxy-6-chloropyridazine.

Melting point: 138° – 140° C, with decomposition

Triethylamine salt of 3-phenyl-4-hydroxy-6-chloropyridazine

N-isobutyl-N-2-cyanoethylamine salt of 3-phenyl-4-hydroxy-6-chloropyridazine.

Melting point: 220° C 3-(2'-ethyl-hexyloxy)-propylamine-(1) salt of 3-phenyl-4-hydroxy-6-chloropyridazine.

In addition, all the remaining active ingredients, of this invention mentioned in the following Examples can be obtained according to the methods of Examples 1–3.

The active ingredients obtained according to Examples 1–3 may be formulated as shown in Example 4.

EXAMPLE 4

20 parts of 3-phenyl-4-hydroxy-6-chloropyridazine were mixed with the equivalent amount of an amine defined in Examples 1–3 and with 5 parts of an alkylarylpolyglycol ether, made up to 100 parts with a diluent such as water, glycerol, cyclohexanone or xylene, and stirred while warming gently until a clear solution was formed. The concentrates thus obtained gave clear solutions or emulsions after stirring into the required amount of water for application to the plants.

EXAMPLE 5

287.6 parts of the methylamine salt and 321.5 parts of the trimethylamine salt of 3-phenyl-4-hydroxy-6-chloropyridazine were ground up with 40 parts of sodium lignin sulphonate, 230.9 parts of siliceous earth and 120 parts of a polyhydroxyethylene-alkyl etherurea complex. This spray powder was suspended in water and sprayed on the plants.

EXAMPLE 6

215.6 parts of the methylamine salt and 241.1 parts of the trimethylamine salt of 3-phenyl-4-hydroxy-6-chloropyridazine were mixed with 381.3 parts of 2-methyl-4-chlorophenoxypropionic acid magnesium salt, and ground up with 30 parts of sodium lignin sulphonate, 31 parts of siliceous earth, and 100 parts of polyhydroxyethylene-alkyl ether-urea complex.

The effect of the amine salts or amine salt mixtures according to the invention on weeds and the compatibility of the compounds as regards food plants will be illustrated in more detail in the following examples.

EXAMPLE 7

Weeds raised in a greenhouse, namely

| | | | |
|---|---|---|---|
| Galium aparine | burdock | = | A |
| Erodium cicutarium | stork's bill | = | B |
| Centaurea jacea | knapweed | = | C |
| Lapsana communis | nipplewort | = | D |
| Anthemis arvensis | corn-camomile | = | E |
| Lamium purpureum | dead nettle | = | F |
| Stellaria media | chickweed | = | G |
| Veronica hederaefolia | speedwell | = | H |
| Galinsoga parviflora | field scabious | = | I |
| Raphanus raphanistrum | jointed charlock | = | K | were sprayed with an aqueous solution or a suspension of the respective amine salt or amine salt mixture according to the invention after the weeds had reached the 4- to 6-leaf stage. The application amount corresponded to 1.0 kg. per hectare based on the free OH—compound. 14 days after the treatment, the herbicidal effect on the weeds was determined according to the EWRC evaluation scale (EWRC = European Weed Research Council). The results are shown in Tables 1 and 2, wherein the ratings 1–9 correspond to the following extermination rates and success evaluations:

| Herbicidal effect rating | Corresponding % extermination | Evaluation of the herbicidal effect |
|---|---|---|
| 1 | 100 | excellent |
| 2 | 97.5 | very good |
| 3 | 95 | good |
| 4 | 90 | satisfactory |
| 5 | 85 | still sufficient |
| 6 | 75 | not sufficient |
| 7 | 65 | slight |
| 8 | 32.5 | very slight |
| 9 | 0 | ineffective |

Table 1

Compounds of the formula I, X = Cl

Herbicidal effect (ratings 1 to 9)

$$\begin{array}{c} R_1 \\ N-R_2 \\ R_3 \end{array}$$

| | B | C | D | A | E | F | G | H | I | K | φ herbicidal effect in % |
|---|---|---|---|---|---|---|---|---|---|---|---|
| Triethylamine | 1 | 3 | 3 | 2 | 2 | 2 | 2 | 2 | 1 | 2 | 97,5 |
| Triethanolamine | 2 | 3 | 3 | 3 | 3 | 3 | 4 | 2 | 2 | 2 | 95.5 |
| Pyrrolidine | 2 | 2 | 2 | 3 | 3 | 3 | 4 | 3 | 3 | 3 | 95.2 |
| Ethanolamine | 2 | 2 | 2 | 3 | 3 | 4 | 3 | 3 | 3 | 3 | 95.2 |
| 2-ethylhexylamine | 2 | 3 | 3 | 3 | 3 | 2 | 3 | 2 | 2 | 3 | 96.0 |
| 3-(2'-ethylhexyl-oxy)propylamine(1) | 1 | 2 | 1 | 1 | 1 | 1 | 2 | 2 | 1 | 2 | 99.0 |
| n-Propylamine | 1 | 2 | 3 | 3 | 2 | 3 | 3 | 4 | 3 | 2 | 95.7 |
| Ethylamine | 1 | 2 | 3 | 3 | 3 | 3 | 3 | 3 | 2 | 3 | 96.0 |
| Diethylamine | 1 | 3 | 2 | 4 | 2 | 2 | 3 | 3 | 3 | 3 | 95.7 |
| Tri-n-propylamine | 1 | 3 | 2 | 3 | 2 | 2 | 2 | 3 | 3 | 3 | 96.5 |
| Tri-n-butylamine | 1 | 3 | 2 | 3 | 2 | 2 | 2 | 3 | 3 | 3 | 96.5 |
| Piperidine | 1 | 3 | 3 | 3 | 3 | 2 | 2 | 3 | 3 | 4 | 95.5 |
| 2-Methylpiperidine | 1 | 3 | 2 | 3 | 3 | 3 | 2 | 3 | 2 | 2 | 96.5 |
| 2,6-Dimethylpiperidine | 1 | 3 | 2 | 2 | 3 | 2 | 3 | 3 | 3 | 3 | 96.2 |
| 2-Ethylpiperidine | 1 | 3 | 2 | 2 | 3 | 3 | 3 | 2 | 3 | 2 | 96.5 |
| Morpholine | 1 | 3 | 2 | 3 | 3 | 3 | 2 | 3 | 2 | 3 | 96.2 |
| Di-n-butylamine | 2 | 3 | 3 | 2 | 3 | 3 | 3 | 2 | 1 | 3 | 96.2 |
| N,N-Dimethyl-ethanolamine | 2 | 3 | 2 | 4 | 2 | 3 | 3 | 3 | 2 | 3 | 95.5 |
| Bis(2-ethylhexyl)amine | 3 | 4 | 4 | 3 | 1 | 3 | 4 | 3 | 2 | 3 | 94.2 |
| Isobutylamine | 2 | 4 | 2 | 2 | 1 | 3 | 3 | 3 | 2 | 4 | 95.5 |
| 2-(N,N-Dimethylamino)-ethylamine | 2 | 4 | 2 | 3 | 1 | 3 | 3 | 3 | 2 | 4 | 95.2 |
| 3-(N,N-Dimethylamino)-propyl-(1)-amine | 2 | 3 | 2 | 4 | 1 | 3 | 3 | 2 | 2 | 3 | 96.0 |
| N,N-Dimethyl-N-tert.-hydroxy-butylamine | 2 | 3 | 2 | 4 | 1 | 2 | 3 | 3 | 3 | 3 | 96.2 |
| 3-(N,N-Dimethylamino)-propyl-(1)-amine | 3 | 4 | 4 | 4 | 1 | 4 | 4 | 3 | 3 | 4 | 92.5 |
| N,N-Dimethyl-N-(3-hydroxy-propyl-(1)-amine | 1 | 3 | 1 | 3 | 1 | 2 | 4 | 2 | 2 | 3 | 96.7 |
| N,N-Di-n-butyl-ethanolamine | 1 | 3 | 1 | 1 | 1 | 2 | 3 | 2 | 1 | 3 | 98.0 |
| N,N-Dimethyl-N-(2-hy- | 1 | 4 | 1 | 2 | 1 | 2 | 3 | 2 | 2 | 3 | 97.0 |

Table 1-continued

Compounds of the formula I, X = Cl
Herbicidal effect (ratings 1 to 9)

$$\begin{array}{c} R_1 \\ N-R_2 \\ R_3 \end{array}$$

| | B | C | D | A | E | F | G | H | I | K | φ herbicidal effect in % |
|---|---|---|---|---|---|---|---|---|---|---|---|
| droxy-isopropyl)-amine | | | | | | | | | | | |
| N-Methyl-cyclohexylamine | 1 | 3 | 1 | 1 | 1 | 2 | 3 | 2 | 1 | 2 | 98.2 |
| Diallylamine | 1 | 2 | 1 | 1 | 1 | 2 | 3 | 3 | 2 | 3 | 97.7 |
| Monomethylamine | 2 | 4 | 1 | 4 | 3 | 3 | 4 | 4 | 2 | 4 | 93.5 |
| Dimethylamine | 1 | 3 | 3 | 3 | 1 | 3 | 3 | 3 | 2 | 3 | 96.2 |
| Trimethylamine | 2 | 4 | 3 | 3 | 3 | 3 | 4 | 2 | 2 | 4 | 94.2 |
| n-Octylamine | 1 | 3 | 1 | 1 | 1 | 2 | 3 | 3 | 2 | 3 | 97.5 |
| n-Decylamine | 1 | 3 | 1 | 1 | 1 | 2 | 3 | 2 | 2 | 3 | 97.7 |
| n-Dodecylamine | 2 | 4 | 4 | 4 | 1 | 3 | 4 | 3 | 3 | 4 | 93.2 |
| Di-isopentylamine | 2 | 4 | 3 | 4 | 1 | 4 | 4 | 3 | 3 | 4 | 93.2 |
| Di-n-octylamine | 1 | 3 | 3 | 3 | 3 | 3 | 3 | 2 | 2 | 3 | 96.0 |
| N-(3-(2'-ethylhexyloxy propyl)-N-(2-cyanoethyl)-amine | 1 | 3 | 1 | 3 | 1 | 3 | 4 | 3 | 2 | 4 | 95.0 |
| N-Methyl-N-(2-cyanoethyl)-amine | 1 | 3 | 1 | 1 | 1 | 2 | 3 | 3 | 2 | 3 | 97.5 |
| N-ethyl-N-(2-cyanoethyl)amine | 1 | 2 | 1 | 1 | 1 | 2 | 3 | 2 | 1 | 3 | 98.2 |
| N-Propyl-N-(2-cyanoethyl)amine | 1 | 1 | 1 | 1 | 1 | 2 | 2 | 2 | 1 | 3 | 98.7 |
| N-Isopropyl-N-(2-cyanoethyl)amine | 1 | 3 | 1 | 1 | 1 | 2 | 3 | 3 | 1 | 3 | 97.7 |
| N-Butyl-N-(2-cyanoethyl)-amine | 1 | 3 | 1 | 3 | 1 | 3 | 4 | 3 | 3 | 4 | 95.5 |
| N-Isobutyl-N-(2-cyanoethyl)-amine | 1 | 3 | 1 | 1 | 1 | 2 | 3 | 3 | 2 | 3 | 97.5 |
| N-(octyl-(1)-N-(2-cyanoethyl)-amine | 1 | 4 | 1 | 1 | 1 | 2 | 3 | 2 | 2 | 3 | 97.2 |
| Methoxyethylamine | 1 | 4 | 2 | 3 | 1 | 4 | 5 | 4 | 2 | 4 | 93.5 |
| 3-Methoxypropyl-(1)-amine | 1 | 4 | 2 | 3 | 1 | 3 | 5 | 4 | 2 | 4 | 94.0 |
| 3-ethoxypropyl-(1)-amine | 1 | 4 | 2 | 4 | 2 | 4 | 5 | 4 | 2 | 4 | 92.7 |
| 3-(n-Butoxy)-propyl-(1)-amine | 1 | 4 | 3 | 3 | 1 | 4 | 4 | 3 | 2 | 3 | 94.7 |
| free OH-compound (comparison substance according to Austrian Patent 309,883) | 5 | 7 | 6 | 6 | 6 | 6 | 7 | 6 | 4 | 6 | 75.5 |
| Diethanolamine + Dimethylamine | 1 | 2 | 1 | 1 | 1 | 1 | 3 | 2 | 1 | 3 | 98.5 |
| Monoethanolamine + Methylamine | 1 | 1 | 1 | 1 | 1 | 2 | 3 | 2 | 1 | 3 | 98.5 |
| Monoethylamine + Triethanolamine | 1 | 1 | 3 | 1 | 1 | 3 | 3 | 3 | 1 | 3 | 97.5 |
| Methylamine + Trimethylamine | 1 | 2 | 1 | 1 | 1 | 1 | 1 | 1 | 1 | 11 | 99.7 |
| Triethanolamine + Trimethylamine | 2 | 4 | 3 | 3 | 1 | 4 | 4 | 3 | 2 | 4 | 94.0 |
| Monoethanolamine + Methylamine + Triethanolamine | 1 | 3 | 1 | 3 | 1 | 3 | 3 | 2 | 2 | 3 | 97.0 |
| Methylamine + Monoethanolamine + Triethanolamine + Trimethylamine | 1 | 3 | 3 | 1 | 1 | 2 | 3 | 3 | 2 | 3 | 97.0 |

Table 2

Compounds of the formula I, X = Br
Herbicidal effect (ratings 1 to 9)

$$\begin{array}{c} R_1 \\ N-R_2 \\ R_3 \end{array}$$

| | B | C | D | A | E | F | G | H | I | K | φ herbicidal effect in % |
|---|---|---|---|---|---|---|---|---|---|---|---|
| Triethylamine | 1 | 3 | 3 | 2 | 2 | 2 | 2 | 2 | 1 | 2 | 97.5 |
| n-Octylamine | 1 | 4 | 1 | 1 | 1 | 3 | 4 | 4 | 3 | 4 | 96.0 |
| N-methyl-N-cyano- | 1 | 2 | 1 | 1 | 1 | 2 | 3 | 2 | 2 | 3 | 98.0 |

Table 2-continued

Compounds of the formula I, X = Br

Herbicidal effect (ratings 1 to 9)

| N< R₁ R₂ R₃ | B | C | D | A | E | F | G | H | I | K | φ herbicidal effect in % |
|---|---|---|---|---|---|---|---|---|---|---|---|
| ethyl-amine | | | | | | | | | | | |

EXAMPLE 8

Wheat, barley, oats, rye, maize and rice were cultivated in a greenhouse. As soon as the plants had formed three leaves they were sprayed with an aqueous solution or suspension of the amine salt or amine salt mixture according to the invention. The amount applied corresponded to 2.0 kg. per hectare, based on to the free OH-compound. The plants were continuously investigated over a period of 3 weeks for any possible harmful effects (burning, growth inhibition). All the amine salts and amine salt mixtures of the formula I specified in Tables 1 and 2 were found to be completely compatible with food plants. No harmful effects were established in any case.

What we claim is:

1. An amine salt of a 3-phenyl-6-halo-4-hydroxypyridazine of the formula

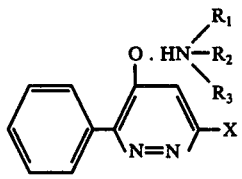

wherein X is selected from the group consisting of chlorine and bromine, $R_1$ is selected from the group consisting of alkyl containing up to 14 carbon atoms, alkenyl containing up to 6 carbon atoms, cycloalkyl containing 5 to 7 carbon atoms, and alkyl contaning up to 14 carbon atoms which is monosubstituted by hydroxy, alkoxy containing up to 10 carbon atoms, cyano, amino, lower monoalkylamino or lower dialkylamino, and $R_2$ and $R_3$ are each selected from the group consisting of hydrogen and the groups defined above with respect to $R_1$, or $R_1$ and $R_2$ together with the nitrogen atom to which they are attached form heterocyclic selected from the group consisting of pyrrolidino pyrrolidino monosubstituted by lower alkyl, pyrrolidino disubstituted by lower alkyl, piperidino, piperidino monosubstituted by lower alkyl and piperidino disubstituted by lower alkyl.

2. The salt according to claim 1, the triethylamine salt of 3-phenyl-6-chloro-4-hydroxypyridazine.

3. The salt according to claim 1, the 3-(2'-ethylhexyloxy)-propylamine salt of 3-phenyl-6-chloro-4-hydroxypyridazine.

4. The salt according to claim 1, the N,N-di-n-butyl-ethanolamine salt of 3-phenyl-6-chloro-4-hydroxypyridazine.

5. The salt according to claim 1, the N,N-dimethyl-N-(2-hydroxyisopropyl)-amine salt of 3-phenyl-6-chloro-4-hydroxypyridazine.

6. The salt according to claim 1, the N-methyl-n-cyclohexylamine salt of 3-phenyl-6-chloro-4-hydroxypyridazine.

7. As salt according to claim 1, the diallylamine salt of 3-phenyl-6-chloro-4-hydroxypyridazine.

8. As salt according to claim 1, the n-octylamine salt of 3-phenyl-6-chloro-4-hydroxypyridazine.

9. As salt according to claim 1, the n-decylamine salt of 3-phenyl-6-chloro-4-hydroxypyridazine.

10. As salt according to claim 1, the N-ethyl-N-(2-cyanoethyl)amine salt of 3-phenyl-6-chloro-4-hydroxypyridazine.

11. As salt according to claim 1, the N-n-propyl-N-(2-cyanoethyl)amine salt of 3-phenyl-6-chloro-4-hydroxypyridazine.

12. As salt according to claim 1, the N-isobutyl-N-(2-cyanoethyl)amine salt of 3-phenyl-6-chloro-4-hydroxypyridazine.

13. As salt according to claim 1, the N-n-ocytyl-N-(2-cyanoethyl) amine salt of 3-phenyl-6-chloro-4-hydroxypyridazine.

14. As salt according to claim 1, the N-methyl-N-(2-cyanoethyl) amine salt of 3-phenyl-6-bromo-4-hydroxypyridazine.

15. A herbicidal composition which comprises at least one amine salt according to claim 1 in admixture with a liquid or solid diluent.

16. A composition according to claim 15, which further comprises at least one known herbicidal agent selected from the group consisting of 2,4-dichlorophenoxyacetic acid, 2-methyl-4-chlorophenoxyacetic acid, 2,4,5-trichlorophenoxyacetic acid, 2-(2-methyl-4chlorophenoxy)-propionic acid, 2-(2,4-dichlorophenoxy)-propionic acid, 4(2-methyl-4chlorophenoxy)-butyric acid, 4(2,4-dichlorophenoxy)-butyric acid, 2-(2,4,5-trichlorophenoxy)-propionic acid, 4-chloro-2-oxobenzothiazolin-3-yl acetic acid, 3,6-dichloro-2-methoxybenzoic acid, amine salts of said compounds and esters of said compounds.

* * * * *